United States Patent
Tontarra et al.

(10) Patent No.: US 9,028,500 B2
(45) Date of Patent: May 12, 2015

(54) SURGICAL INSTRUMENT

(75) Inventors: Thomas Tontarra, Wurmlingen (DE); Alberto Petrella, Wurmlingen (DE)

(73) Assignee: Thomas Tontarra Grundstuecksverwaltungs GmbH & Co. KG, Wurmlingen (DE)

( * ) Notice: Subject to any disclaimer, the term of this patent is extended or adjusted under 35 U.S.C. 154(b) by 553 days.

(21) Appl. No.: 12/925,424

(22) Filed: Oct. 21, 2010

(65) Prior Publication Data

US 2011/0106065 A1     May 5, 2011

(30) Foreign Application Priority Data

Oct. 22, 2009    (DE) .......................... 20 2009 014 310

(51) Int. Cl.
    *A61B 17/00*       (2006.01)
    *A61B 18/18*       (2006.01)
    *A61B 17/32*       (2006.01)
    *A61B 17/16*       (2006.01)
    *A61B 19/00*       (2006.01)

(52) U.S. Cl.
    CPC ............. *A61B 17/1611* (2013.01); *A61B 19/34* (2013.01); *A61B 2019/4868* (2013.01)

(58) Field of Classification Search
    USPC .................. 606/1, 79, 83, 169–171, 205–208
    See application file for complete search history.

(56) References Cited

U.S. PATENT DOCUMENTS

| | | | |
|---|---|---|---|
| 5,304,203 A | 4/1994 | El-Mallawany et al. | |
| 5,306,285 A | 4/1994 | Miller et al. | |
| 5,366,477 A * | 11/1994 | LeMarie et al. | 606/208 |
| 5,411,481 A | 5/1995 | Allen et al. | |
| 5,584,855 A | 12/1996 | Onik | |
| 5,653,713 A * | 8/1997 | Michelson | 606/83 |
| 5,674,220 A | 10/1997 | Fox et al. | |
| 5,797,941 A | 8/1998 | Schulze et al. | |
| D410,542 S | 6/1999 | McCool et al. | |
| 6,254,623 B1 | 7/2001 | Haibel, Jr. et al. | |
| 6,325,811 B1 | 12/2001 | Messerly | |
| 6,623,482 B2 | 9/2003 | Pendekanti et al. | |
| 6,991,633 B2 | 1/2006 | Agbodoe | |

(Continued)

FOREIGN PATENT DOCUMENTS

| | | |
|---|---|---|
| DE | 297 18 969 U1 | 3/1998 |
| DE | 199 49 422 A1 | 4/2001 |
| DE | 20 2009 001 811 U1 | 6/2009 |

OTHER PUBLICATIONS

U.S. Appl. No. 29/349,936, inventor Thomas Tontarra, filed May 20, 2010.

*Primary Examiner* — Lynsey Crandall
*Assistant Examiner* — William Cheng
(74) *Attorney, Agent, or Firm* — Kriegsman & Kriegsman (57) ABSTRACT

The invention relates to a surgical instrument, in particular a sliding shaft instrument, with a main part, and a moveable part relative thereto, with a handle attached to the main part, comprising a fixed grip and a grip actuating the moveable part, with at least one guide, through which, in relation to the main part, the moveable part is moveable between an initial position and a working position, and with a sliding surface attached to the movable part and pointing towards the main part, the sliding surface being slid along a guide surface attached to the main part and pointing towards the sliding surface, with at least the sliding surface or the guide surface are assigned to each other for the formation of a washable gap.

10 Claims, 7 Drawing Sheets

(56) References Cited

U.S. PATENT DOCUMENTS

| | | |
|---|---|---|
| D535,027 S | 1/2007 | James et al. |
| 7,316,703 B2 | 1/2008 | Suzuki |
| 7,377,933 B2 | 5/2008 | Martin |
| D612,050 S | 3/2010 | Baynham |
| D613,407 S | 4/2010 | Baynham |
| 7,695,485 B2 | 4/2010 | Whitman et al. |
| 7,749,222 B2 | 7/2010 | Lu et al. |
| D637,880 S | 5/2011 | Kenny et al. |
| D640,790 S | 6/2011 | Nishimura |
| D646,389 S | 10/2011 | Claypool et al. |
| 8,092,488 B2 | 1/2012 | DiNucci |
| 8,246,622 B2 | 8/2012 | Siegal et al. |
| 8,252,021 B2 | 8/2012 | Boulnois et al. |
| 2006/0122615 A1* | 6/2006 | McKinley ............ 606/83 |
| 2007/0093843 A1* | 4/2007 | Schneiter ............ 606/83 |

* cited by examiner

SURGICAL INSTRUMENT

The invention relates to a surgical instrument, in particular a sliding shaft instrument, with a main part, and a moveable part relative thereto, with a handle attached to the main part, comprising a fixed grip and a grip actuating the moveable part, with at least one guide, through which, in relation to the main part, the moveable part is moveable between an initial position and a working position, and with a sliding surface arranged on the movable part and pointing towards the main part, the sliding surface being slidable along a guide surface arranged on the main part and pointing towards the sliding surface.

Surgical instruments of this type are used, for example, in the removal of tissues, bones or similar. At the outset of development of surgical instruments of this type, these surgical instruments were not able to be dismantled. Thus there was a disadvantage in that after a surgical procedure, these surgical instruments could not be completely cleaned and sterilised, particularly in the region of the guides between the moveable part and the main part, as well as between the sliding and guide surfaces of the moveable part and the main part.

A bone punch which is able to be dismantled is known in DE 297 18 969 U1, in which, on the actuatable grip pointing to the moveable part, an open-edged slit is formed, which engages into a recess in the moveable part in order to incorporate a pivot fixed thereto. Through a detachable arrangement of the spring element between the actuatable grip and the fixed grip, it can be made possible for the actuatable grip to be further expandable from a rest position, and therefore moves the moveable part further backwards towards the main part, so that the pilot pins of the moveable part are released from the guide of the main part. In connection to this, the moveable part can be removed from the main part, whereby both parts can be cleaned separately and subsequently sterilised. This arrangement is disadvantageous in that the dismantling and assembly are time-consuming. Additionally, there is also the problem that when several surgical instruments are cleaned simultaneously, the allocation of the respective moveable part to the shaft is time-consuming. This allocation is necessary, therefore, since the main part and the moveable part are brought to a collective finishing operation, and on a mix-up of the moveable parts in the region of the gap, which is formed by the sliding surface and the guide surface, overhangs can occur, which can result in injuries.

In order to avoid this disadvantage, a surgical instrument is known in DE 199 49 422 A1 in which, indeed, it is made possible to remove the moveable part from the main part for cleaning the surgical instrument, however the moveable part remains firmly attached to the main part by a hinge joint. Therefore, the problem of allocating the moveable parts to the respective main parts is eliminated. However, the necessary expenditure of time remains in order to separate the moveable part from the main part, in order to clean and to sterilise the surgical instrument, as well as the subsequent assembly.

Therefore, the object of the invention is to create a surgical instrument, in particular a sliding shaft instrument, which facilitates cleaning and sterilisation, without requiring the surgical instrument to be dismantled, also even partly, for the cleaning process.

This object is achieved by a surgical instrument having a sliding shaft instrument, with a main part and a relative moveable part, with a handle arranged on the main part, the former having a fixed grip and a grip for actuating the moveable part, with at least one guide through which the moveable part relative to the main part is moveable between an initial position and a working position, and with a sliding surface pointing to the main part and arranged on the moveable part, the sliding surface being slidable along the guide surface, pointing to the sliding surface and arranged on the main part and at least the sliding surface or the guide surface are arranged with each other for the formation of a washable gap.

Further advantageous embodiments and further developments are given in the further dependent claims.

The embodiment of the surgical instrument according to the invention, in which at least the sliding surface of the moveable part or the guide surface of the main part are reduced to a width for forming a washable gap, has the advantage that after use of the surgical instrument, no further handles are required in order to dismantle the surgical instrument, so that this surgical instrument can be cleaned and sterilised. A subsequent assembly for the next use is also omitted. Therefore cleaning of the surgical instrument is possible without dismantling.

Furthermore, the embodiment according to the invention has the advantage that through the reduction of the sliding and guide surfaces which border each other, a reduction of the sliding friction force between the main part and the moveable part is also made possible, whereby an improvement of the operating characteristics or a smoother movement of the moveable part to the main part is given. The same is valid for the allocation to each other for the formation of a washable gap. The same applies for any combination of these alternatives.

Furthermore, the embodiment according to the invention makes it possible that the crucial regions of a surgical instrument, in which bacteria accumulate, are accessible, or can be washed in a washing machine with washing water, and preferably subsequently sterilised. Therefore the dismantling of the surgical instrument is unnecessary.

In a further preferred embodiment of the invention, it is intended that at least the guide surface or the sliding surface is open in a spatial direction. A preferred spatial direction is in a longitudinal direction, or in a transverse longitudinal direction of the main part and moveable part, whereby the spatial direction preferably lies in a parting plane between the main part and the moveable part. This represents a first simple embodiment, and facilitates the maintenance of the present operation of the surgical instrument. In this embodiment, this takes place particularly through the opening of at least the guide surface or sliding surface in a spatial direction, for example in the form of a recess.

In a further preferred embodiment of the invention, it is intended that at least the sliding surface or the guide surface are assigned to each other for the formation of a washable gap. Therefore, inter alia, a jet action can take place in a washing process, in order to improve the cleaning. In this embodiment, at least the surface portions bordering each other between the sliding surface and the guide surface are so reduced, that on cleaning the surgical instrument in a washing machine, the spray streams used in the cleaning process suffice, if necessary, in order to wash out bacteria or other impurities found in this gap.

According to a preferred embodiment of the invention, at least one bevel bordering the guide surface or the sliding surface is provided on at least one external side of the main part or the moveable part, the bevel being inclined at least in portions to the longitudinal centre line. Therefore the width of the sliding surface and/or the guide surface is reduced. For example, for a bevel arranged on the moveable part, the edge formed between the sliding surface and the bevel is positioned inward or towards the longitudinal centre line opposite the edge between the guide surface and an external side of the main part, so that seen in cross-section, a relief develops, in particular a recess in triangular form. Therefore, on impact of a spray stream on the surgical instrument, the spray stream is led towards the gap between the sliding surface and the guide surface, so that an improved cleaning of the gap or the opening or recess is made possible. This effect is particularly improved, then, if a bevel of this type is arranged symmetrically about the cleavage plane, which is formed by the sliding and guide surfaces. Therefore the spray stream can be targeted to the gap. Simultaneously, when using a surgical instrument of this type, there is no damage caused to the tissues surrounding the shaft.

According to a further preferred embodiment of the invention, a bevel is provided on each external side bordering the sliding or guide surface, and this bevel is formed preferably mirror-symmetrically about the longitudinal centre line, and in particular, to the gap. Therefore, for example, seen in cross-section, a geometry in the form of a truncated cone can be formed, whereby the gap width between the sliding surface and the guide surface can be considerably reduced compared to surgical instruments according to the prior art. In this way, the reduced width of the bevel and this reduced width of the guide surface can be provided equally or differing from each other.

Furthermore, it is preferable that a bevel is provided on only one external side, with the bevel substantially extending over the whole width of the main part or moveable part, so that the sliding surface and guide surface directly border an external are reduced in width to form a washable gap. This embodiment has the advantage that a maximal size of orifice or incoming area for the spraying liquid is given in the remaining gap between the main part and the moveable part. Additionally, the opposite external side can be designed as almost closed.

In a further preferred embodiment, it is intended that at least the sliding surface or guide surface is opened by a recess extending transversely across the longitudinal extent of the main part and moveable part. Through recesses of this type, the gap formed between the moveable part and the main part is completely disconnected. Thus this region is particularly easy to clean. Preferably, between the guides and/or hinge joints, and in particular recesses extending across the longitudinal extent of the main part and moveable part are provided at least in portions in the sliding surface and/or the guide surface.

In an alternative embodiment of the invention, it is intended that at least the sliding surface or the guide surface is opened by a recess extending in a longitudinal direction of the main part and moveable part. This alternative embodiment has the advantage that the surgical instrument, in particular the sliding shaft, can maintain the current appearance of conventional surgical instruments, that is to say, that the external sides of the moveable part and the main part are merged into one another in a flush manner, however the advantages of the invention are given. In this way, for example, a recess in the form of a longitudinal channel or through-channel can be formed, whereby the cleaning and spraying liquids are introduced at the proximal or distal end, and are brought out at the opposite side in each case. Simultaneously, a side release over the remaining and washable gap between the sliding surface and the guide surface can take place.

In an advantageous further development, it is intended that the recess has an undulating form. Therefore, larger regions on the sliding or guide surface to the opposite surface or on both surfaces can be omitted, and thus are easily accessible for cleaning. Alternatively, the recesses can have a triangular, rectangular, trapezoidal, hemispherical or sawtooth form. Recesses of this type are particularly formed in this way, in that these deepen from the sliding or guide surfaces from the moveable part or the main part. This embodiment makes it possible that the opposite external side of the moveable part or main part has a closed top, and a sufficient full cross-section remains, in order to cut tendons or to facilitate the cutting of tissues or similar. The recesses can be uniform or can be combined with each other.

In an alternative embodiment for the recesses, it is intended that these are designed between two elevations arranged so that they are neighbouring each other, which are in a truncated cone form, frustropyramidal form, hemispherical form or in the form of a crescent segment. Therefore, further geometric alternatives for the production of the recess are given, which facilitate easy cleaning as well as a lower control force for actuating the surgical instrument.

According to a further preferred embodiment of the invention, it is intended that at least one recess or a bevel borders a guide. In the process, the guide between the moveable part and the main part can consist of, for example, a T-shaped guiding groove or a similarly shaped guiding groove on the one hand, and on the other hand, a complementary designed pilot pin is intended. Furthermore, the guide can be formed by a hinge joint or a double joint between an actuatable grip and the moveable part. Through the adjacency of the recess or the bevel to the guide, it is ensured that these regions are accessible for the cleaning liquid and the subsequent disinfection.

The invention as well as further advantageous embodiments and further developments of the same are described in more detail and explained below by means of the examples represented in the drawings. The features to be taken from the description and the drawings can be applied individually or in any combination according to the invention. In the drawings:

A first embodiment of a surgical instrument 11 according to the invention is shown in FIG. 1 and FIGS. 2 through 4. This surgical instrument 11, relates to a sliding shaft instrument, for example, a so-called punch, in particular Kerrison punch, which is used in surgical procedures for the removal of bone tissues or similar. The invention is not limited to these punches, but can be applied to all surgical instruments which have the same problems regarding cleaning and sterilisation.

Figure 1:
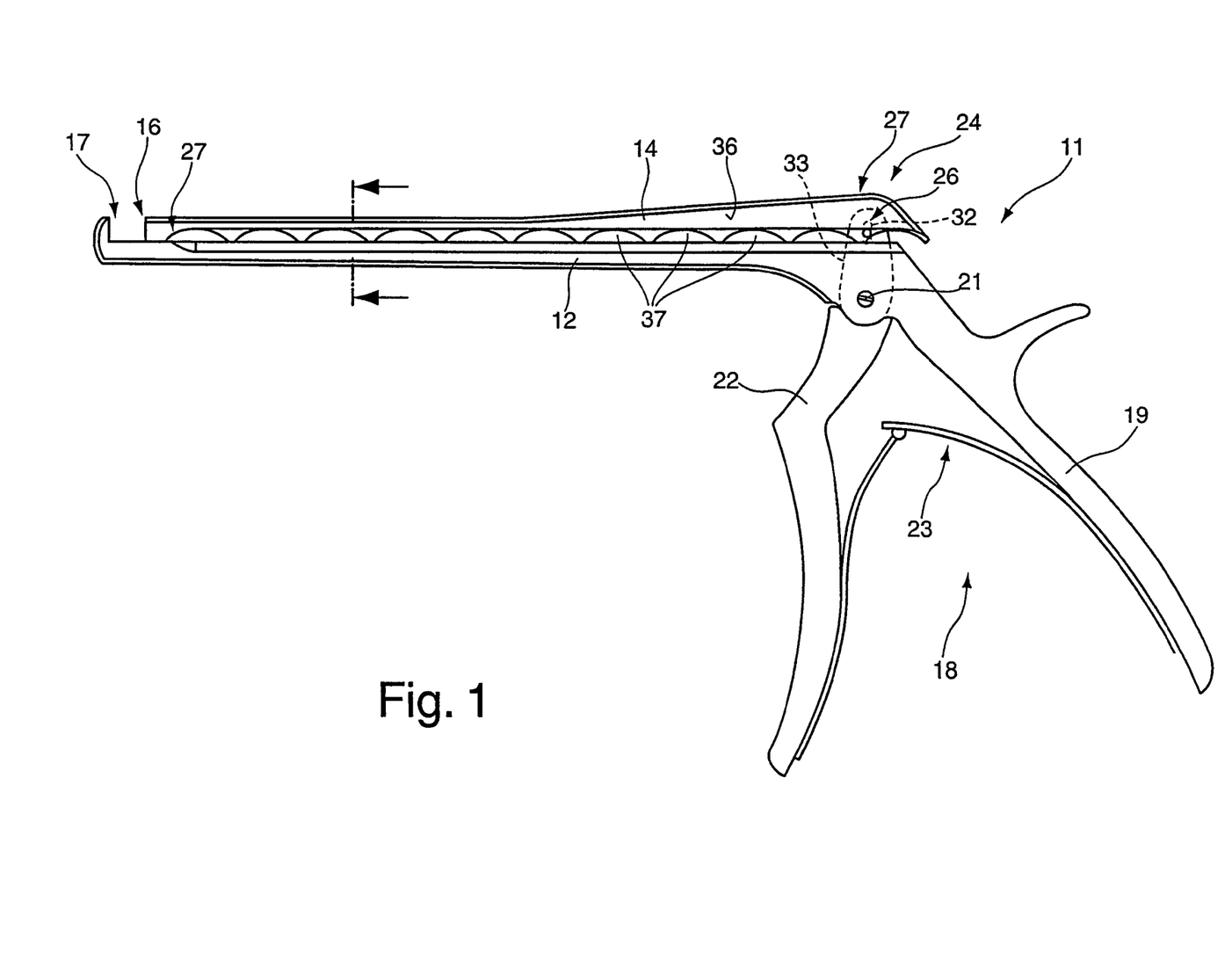
FIG. 1 shows a schematic side view of a surgical instrument according to the invention.

The surgical instrument 11 has a main part 12, which is also referred to as a shaft. This main part 12 incorporates a moveable part 14, which is slidable relative to the main part 12. The moveable part 14 is also named as a slide. Functional elements 16, 17 are provided at the proximal end of the main part 12 and the moveable part 12. This can be a blade and a counter plate or counter-cutter, for example. Equally, in other embodiments, this can be a scissor-type cutting tool, a spatula-shaped cutting tool or grasping forceps or similar. The arrangement of the functional elements 16, 17 is custom designed for the surgical procedure.

A handle 18 is arranged on the main part 12. The main part 12 transitions into a fixed grip 19, and in the transition region from the main part 12 to the fixed grip 19 has a pivot 21, around which an actuatable grip 22 is swivel-mounted. As shown in FIG. 1, the actuatable grip 22 and fixed grip 19 are assigned to each other in an initial position 24 by a spring element 23. In this initial position 24, for example, the functional elements 16, 17 are spaced apart from each other. The represented grip, as well as a ring handle or further variants of grip can be understood by handle 18.

On actuating the grip 22, this is swung about the pivot 21, with the moveable part 14 being moved to the left in order to move the functional element 16 to the functional element 17. A working position is achieved as soon as these are resting against each other. As soon as the actuatable handle 18 is released, the moveable part 14 is moved independently back to the initial position 24 due to the spring force of the spring element 23.

Figure 4:
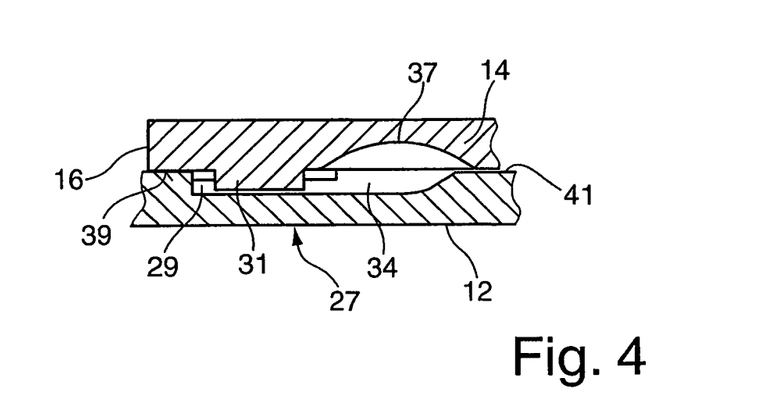
FIG. 4 shows a further schematic enlarged section view of the surgical instrument according to FIG. 1.

The moveable part 14 is led by a hinge joint 26 to the distal end of the surgical instrument 11, and has at the proximal end, for example, a guide 27, which is represented in more detail in FIG. 4 Alternatively, a guide can only be intended in the central region of the main part 12 and moveable part 14, or also there can be an additional guide. For example, a T-groove indentation 29 is intended as a guide 27 on the main part 12, in which a pilot pin 31 is engaged, and is longitudinally displaceable therein. Bordering the indentation 29, an input region 34 is provided, which facilitates the insertion of the pilot pin 31 into the indentation 29 on the completion of the moveable part 14 to the main part 12. After the moveable part 14 is positioned to the main part 12, the further guide 27 is produced, for example, as a hinge joint 26, in which, for example, a pin or screw is made through the moveable part 14 for passage through a recess 32, in particular an oblong hole, in a bracket 33 of the actuatable grip 22. In connection, the pin or the screw can be slurred with an external side 36. A detachable arrangement of the hinge joint 26 for removing the moveable part 14 from the main part 12 for the cleaning and sterilising of the surgical instrument 11 is not possible, and is also not necessary due to the embodiment of the surgical instrument according to the invention.

Figure 2:
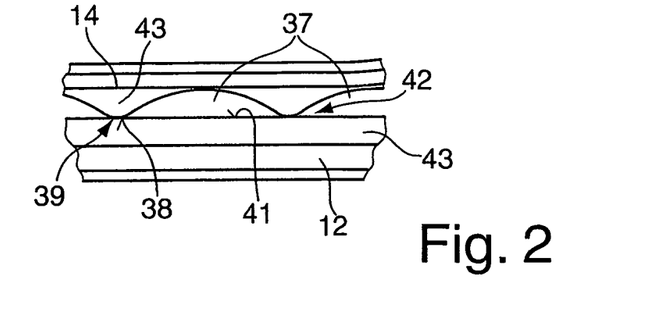
FIG. 2 shows a schematic enlarged side view of the surgical instrument according to FIG. 1.
Figure 3:
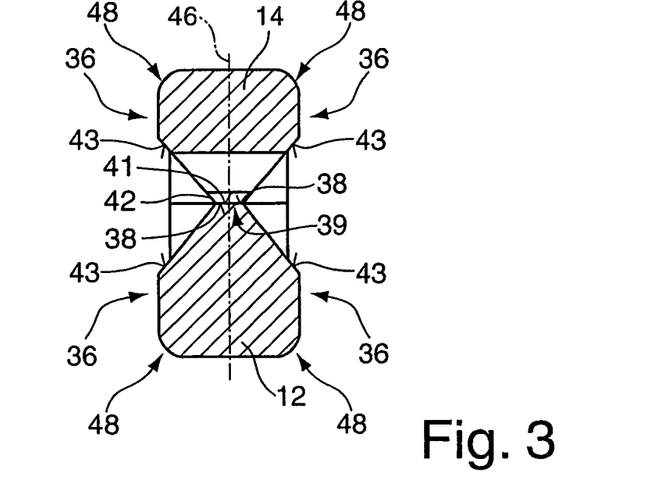
FIG. 3 shows a schematic enlarged section view of the surgical instrument according to FIG. 1.

A first embodiment of the surgical instrument 11 according to the invention is shown enlarged in FIGS. 2, 3 and 4. The main part 12 has a guide surface 41 pointing to the moveable part 14. Opposite this, a sliding surface 39 is assigned to the moveable part 14. During a displacement movement of the moveable part relative to the main part 12, the sliding surface 39 can be moved along the guide surface 41, whereby the sliding surface 39 and the guide surface 41 can be arranged with each other for the formation of a small gap 42, or also lying on each other, at least in portions, or also completely lying against each other. In this first embodiment, for example, the moveable part 14 has a sliding surface 39, which is open in at least a spatial direction. In this case, the moveable part 14 is opened or disconnected by a recess 37 which is transverse in a longitudinal direction of the moveable part 14. According to FIG. 2, this recess 37 is crescent shaped. Preferably, several recesses 37 are installed next to each other, so that these recesses 37 extend from a proximal end of the moveable part 14 to the distal end of the moveable part 14. Thus it is particularly intended that the proximal recess reaches at least to the guide 27, or at least makes this partly accessible from outside. The same is valid for the hinge joint 26 in the distal region, so that this is also easily accessible for cleaning.

Surface portions 38 of the sliding surface 39 of the moveable part 14 are formed between the recesses 37. The sliding surface 39 is considerably reduced by these surface portions 38 compared to conventional surgical instruments, where a continuous sliding surface 39 is provided between the proximal and distal ends of the moveable part 14. Opposite the sliding surface 39, a guide surface 41 is provided on the main part 12. In the embodiment, this guide surface 41 is constructed in a continuous manner with the exception of the indentation 29 and the input region 34 bordering the indentation 29, and a distal end region, in which the bracket 33 of the actuatable grip 22 is arranged for actuating the surgical instrument 11. Alternatively, it can be intended that the guide surface 41 features analogous recesses 37, or the sliding surface 39 and the guide surface 41 feature recesses 37. Alternatively it can be intended that the moveable part 14 has a continuous sliding surface 39 and the recesses 37 are only provided on the guide surface 41. Equally, this can be intended alternately, so that a region of recesses 37 is provided on the guide surface 41, subsequently a region with recesses 37 on the sliding surface 39, and further subsequently a region with recesses on the guide surface 41. Combinations and arrangements are selectable in any way.

Through the embodiment of recesses 37 of this type, it is achieved that the surface portions 38 lying in between them are very small, at least seen in the length in a longitudinal direction of the main part 12, with only very narrow gaps 42 being formed between the sliding surface 39 and the guide surface 41. Through this, a good and easier cleaning is made possible. A rinsing of the gap 42 is also achieved simultaneously. Additionally, a visual check of the cleanliness is given. A surgical instrument 11 of this type also has good operating characteristics. Preferably, the sliding and/or guide surfaces 39, 41 are reduced to a width of less than 70%, in particular less than 90% with regard to the width of the main part 12, or of the moveable part 14, or reduced by both. A punctiform or linear allocation of the sliding and guide surfaces 39, 41 to each other can also be provided.

Complementing these recesses 37, on one or both external sides 36 of the moveable part 14 and/or the main part 12, a bevel 43 can be provided, which in dependence upon the incline, determines the remaining width of the surface portions 38 of the sliding surface 39. Preferably, bevels 43 of this type are provided symmetrically about the central axis 46 of the main part 12 and moveable part 14, so that both external sides 36 are equally formed. Provided that the bevels 43 are only arranged on the moveable part 14, for example, a triangular shaped hook results, whereby on spraying the surgical instrument 11, a type of supply channel for rinsing the gaps 42 is given. The arrangement described above can analogously also only be attached to the main part 12. The preferred embodiment according to FIG. 2b shows that the bevels are not only arranged symmetrically about the central axis 46, but also about the main part 12 and the moveable part 14. Through this, a particularly preferable funnel-shaped arrangement for the supply of the cleaning agent for cleaning the gaps 42 is given. The course of the bevel 43 as straight is only as an example. Further geometries are equally possible.

For example, in FIG. 3, the width of the guide surface 41, which is preferably continuously formed from the distal to the proximal end of the main part 12, is formed as the same width as the surface portions 38 of the sliding surface 39. Alternatively, one of both surfaces 39, 41 can be constructed with a larger or smaller width. Additionally, it can be intended, that for example, one of both surfaces 39, 41 is not constructed in a planar manner, so that for example, planar surface portions 38 of the sliding surface 39 lie on a rounded guide surface 41.

The cross-sections shown of the moveable part 14 and the main part 12 are only for example shown as a square or rectangular formed surface portion with rounded outer edges 48. These geometries can be developed in any way.

It is intended in an alternative embodiment not represented in detail that the main part 12 and the moveable part 14, have in each case a cross-section according to FIG. 3, whereby the recesses 37 are not introduced. An alternative embodiment of this type also makes it possible to completely clean and sterilise the surgical instrument 11 without disassembly. The gap 42, formed between the continuous sliding surface 39 in a longitudinal direction, and equally continuous guide surface 41, is small and cleanable in such a way that if necessary, bacteria accumulating therein can be washed out. Furthermore, it is preferably intended that the width of the sliding surface 39 is formed as smaller than the width of the input region 34, so that this region and the guide 27 can also be cleaned themselves. Additionally, the guides 27 for the slidable arrangement of the moveable part 14 to the main part 12 can be arranged in such a way that a lower gap height is formed.

Figure 5:
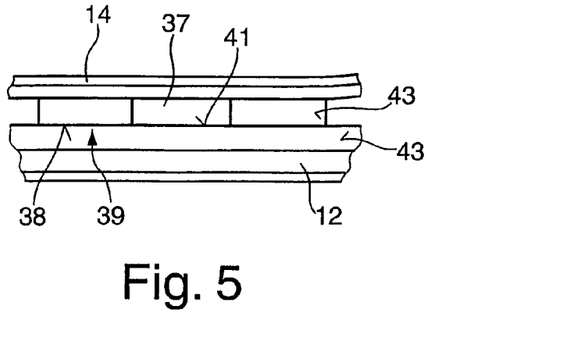
FIG. 5 shows a schematic enlarged side view of an embodiment alternative to FIGS. 2, 3 and 4.
Figure 6:
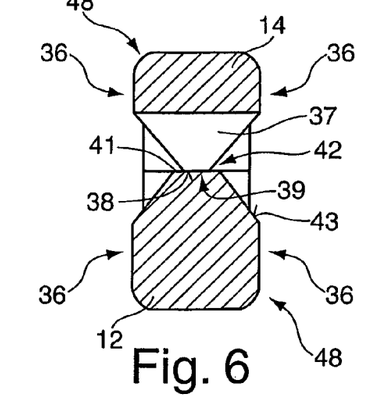
FIG. 6 shows a schematic enlarged section view of the embodiment alternative to FIG. 5.

An embodiment alternative to FIGS. 2 and 3 is shown in FIGS. 5 and 6. In this embodiment it is intended that the recess 37 or recesses 37 are constructed in rectangular form. The surface portions remaining between the recesses 37 are again formed to be small due to the bevels 43 arranged on them. Then, for example, narrow, rectangular shaped surface portions 38 of the sliding surface 39 are constructed, which are oriented in a longitudinal extent of the surgical instrument 11. The guide surface 41 is constructed, for example, wider than the surface portions 38 of the sliding surface 39.

Figure 7:
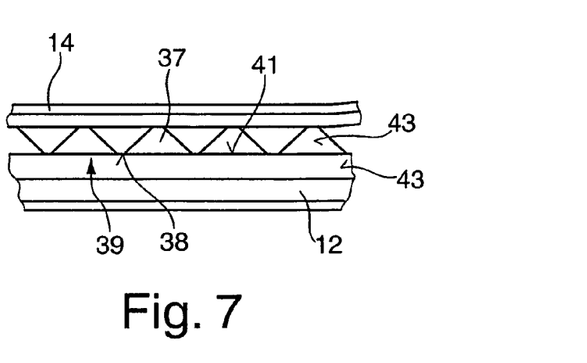
FIG. 7 shows a schematic enlarged side view of an embodiment alternative to FIGS. 2, 3 and 4.
Figure 8:
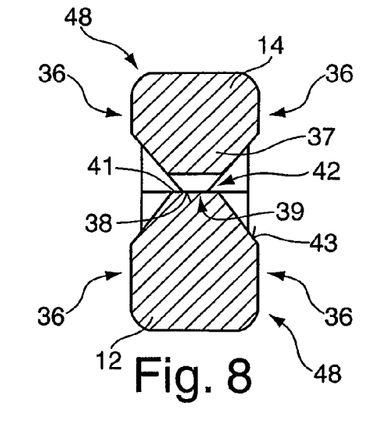
FIG. 8 shows a schematic enlarged section view of the embodiment alternative to FIG. 7.

A further embodiment alternative to FIGS. 2 and 3 is shown in FIGS. 7 and 8. In this embodiment it is intended that the recess 37 is a zigzag shape or a triangular shape. Therefore once again a sufficiently larger free space between the moveable part 14 and the main part 12 can be formed, in order to form washable gaps 42 between the surface portions 38 of the sliding surface 39 and the guide surface 41.

Figure 9:
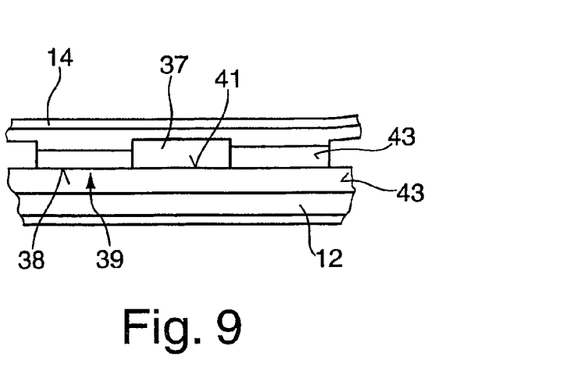
FIG. 9 shows a schematic enlarged side view of an embodiment alternative to FIGS. 2, 3 and 4.
Figure 10:
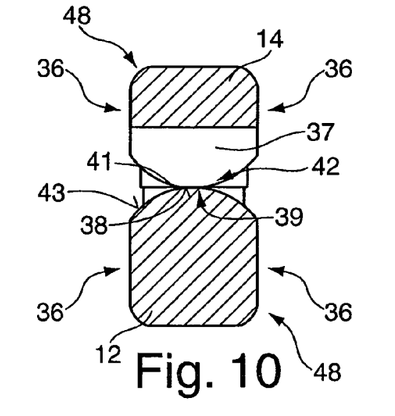
FIG. 10 shows a schematic enlarged section view of the embodiment alternative to FIG. 9.

A further embodiment alternative to FIGS. 2 and 3 is shown in FIGS. 9 and 10. In this, it is intended that in the place of the straight running bevel 43, a crescent-segment curve is constructed, so that the surface portions 38 of the sliding surface 39 lie almost in a line on the guide surface 41. Once again, recesses 37 are formed lying in between, which are represented in this embodiment as rectangular shaped recesses 37. Alternatively, arc shaped, triangular shaped forms or also further geometric forms can be equally intended.

Figure 11:
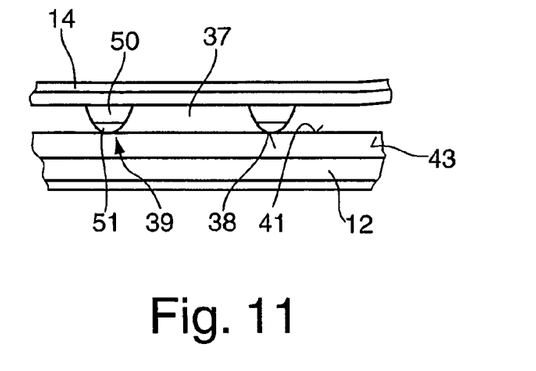
FIG. 11 shows a schematic enlarged side view of an embodiment alternative to FIGS. 2, 3 and 4.
Figure 12:
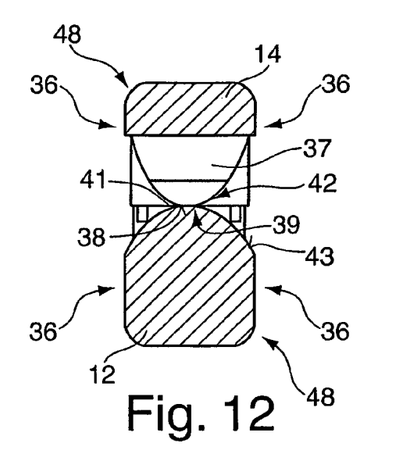
FIG. 12 shows a schematic enlarged section view of the embodiment alternative to FIG. 11.

A further embodiment alternative to FIGS. 2 and 3 is shown in FIGS. 11 and 12. In this embodiment it is intended that the recess 37 is formed by two truncated cone shaped elevations 50, which feature a rounded tip 51, at which the surface portion 38 of the sliding surface 39 is provided, which faces the main part 12 over the guide portion. In the process, the guide surface 41 is provided first of all with a bevel 43, from the external side 36, whereby both the bevels 43 sloping from outside to inside are connected to each other by a curvature or by a domed embodiment of the guide surface 41.

Figure 13:
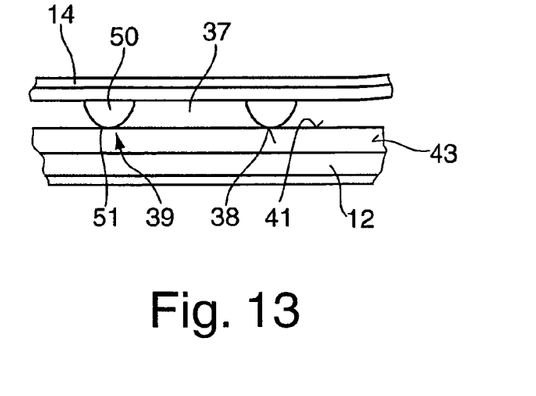
FIG. 13 shows a schematic enlarged side view of an embodiment alternative to FIGS. 2, 3 and 4.
Figure 14:
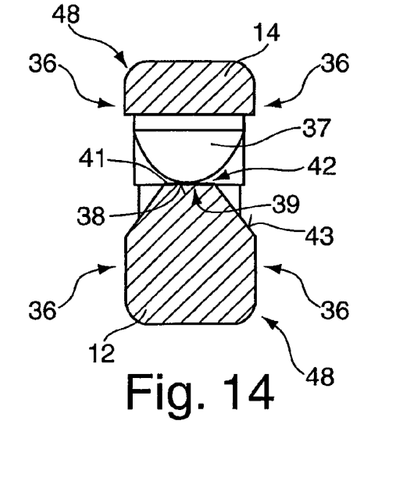
FIG. 14 shows a schematic enlarged section view of the embodiment alternative to FIG. 13.

A further embodiment alternative to FIGS. 11 and 12 is shown in FIGS. 13 and 14. In the process it is intended that the elevations 50 are constructed in a semicircular form, and the guide surface 41 is a planar surface. The width of the guide surface 41 of the main part 12 is again limited by the bevels 43.

Figure 15:
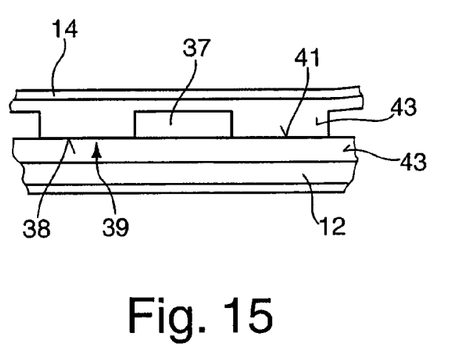
FIG. 15 shows a schematic enlarged side view of an embodiment alternative to FIG. 2, 3 and 4.
Figure 16:
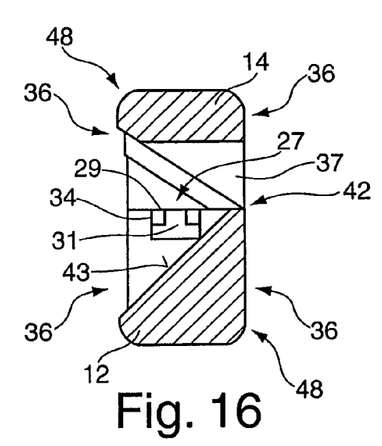
FIG. 16 shows a schematic enlarged section view of the embodiment alternative to FIG. 15.

A further alternative embodiment is included in FIGS. 15 and 16. This embodiment is characterised by a bevel 43 which extends to the moveable part 14 from an external side 36 almost to the other external side 36. Additional recesses 37 with different geometries can be intended in between. Provided that a bevel 43 of this type is provided on the moveable part 14 and preferably also on the main part 12, the remaining gap 42 is reduced to a minimum, with the gap bordering an external side 36 of the main part 12 and the moveable part 14. Through this, it is made possible simultaneously for the indentation 39 of the guide 37 to be freely accessible. The embodiment can also be arranged rotated by 180°.

Figure 17:
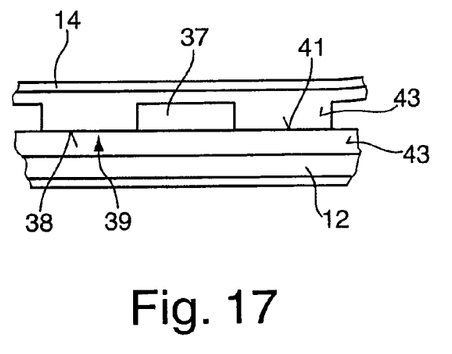
FIG. 17 shows a schematic enlarged side view of an embodiment alternative to FIGS. 2, 3 and 4.
Figure 18:
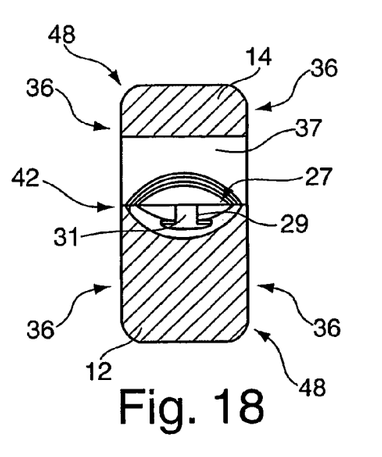
FIG. 18 shows a schematic enlarged section view of the embodiment alternative to FIG. 17.

A further alternative embodiment is included in FIGS. 17 and 18. This embodiment features a concave sliding surface 39 and a concave guide surface 41, whereby two gaps 42 bordering the external side 36 are formed. For the cleaning of a middle channel of this type, again recesses 37 are provided, preferably running transversely, which for example are formed as rectangular shaped recesses 37. It is a matter of course that also only one of both surfaces 39, 41 can feature a concave embodiment. Equally, further geometric recesses can be introduced, in order to obtain an analogous construction of this type according to the sectional representation in FIG. 9b.

The above-mentioned embodiments show that any combinations in the geometry of the guide surfaces 41 and the sliding surface 39 are possible to form a washable gap 42, which remains between the recesses 37.

Figure 19:
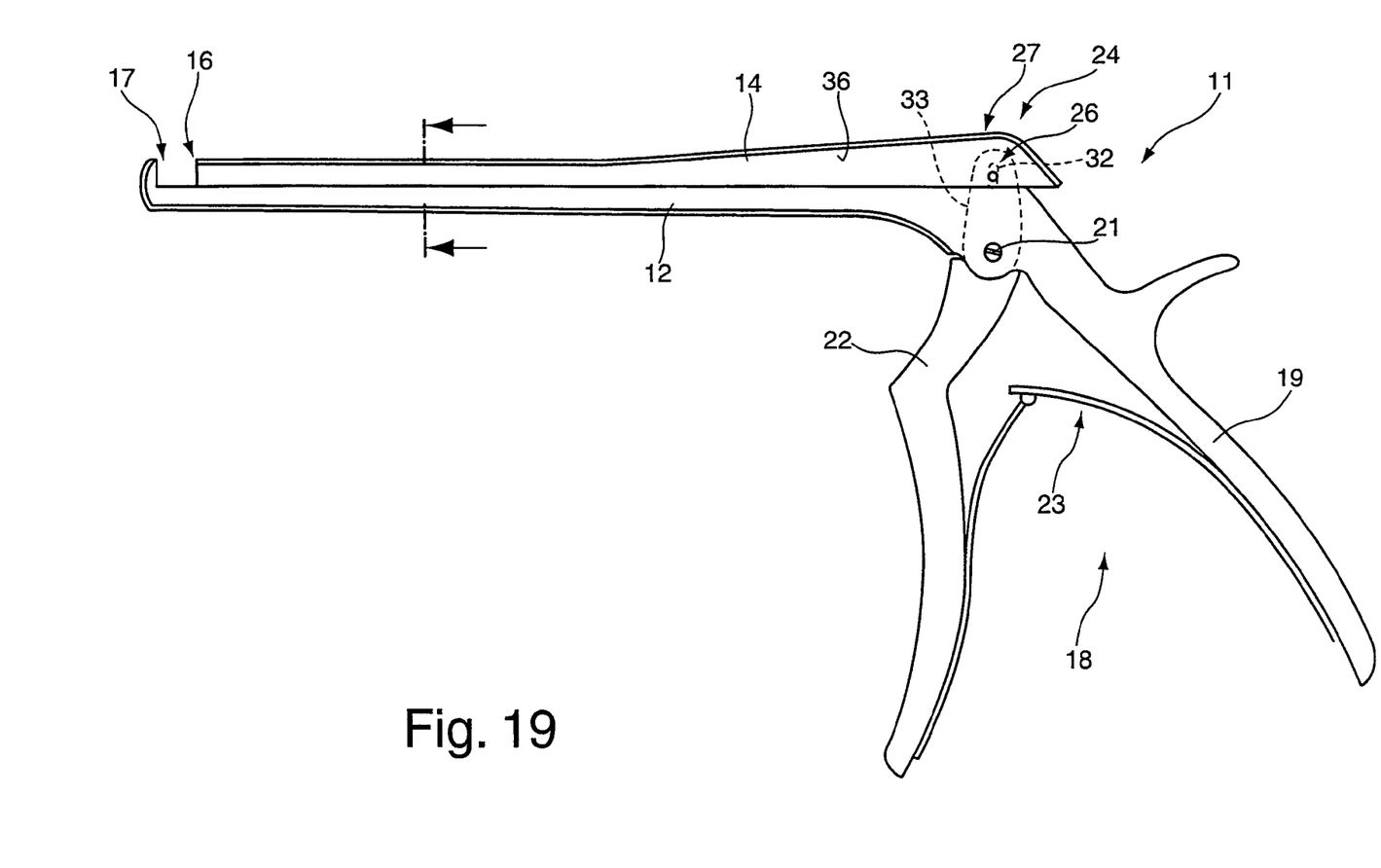
FIG. 19 shows a schematic side view of an alternative embodiment of a surgical instrument according to FIG. 1.
Figure 20:
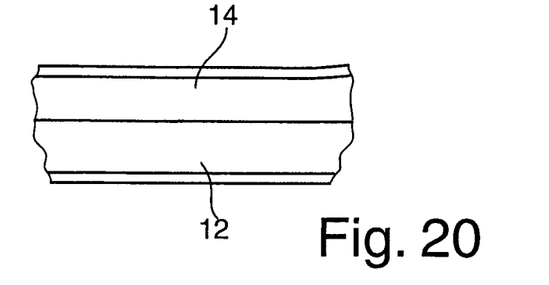
FIG. 20 shows a schematic enlarged side view of the surgical instrument according to FIG. 19.
Figure 21:
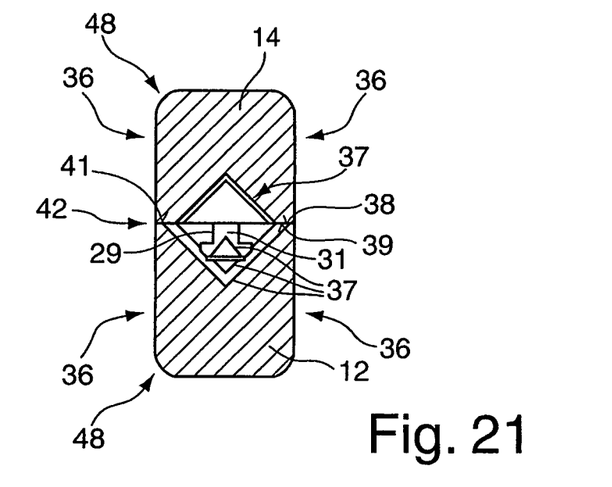
FIG. 21 shows a schematic enlarged section view of the surgical instrument according to FIG. 19.
Figure 22:
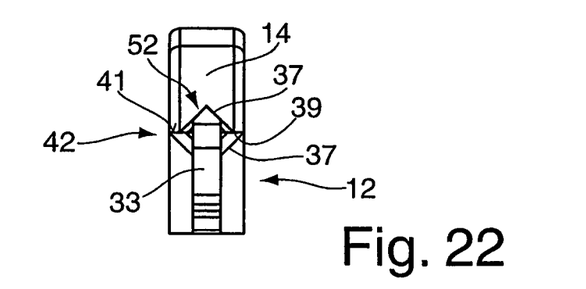
FIG. 22 shows a partial schematic rear view of the surgical instrument according to FIG. 19.

An embodiment of a surgical instrument 11 alternative to FIG. 1 is shown in FIG. 19. In this alternative embodiment, the sliding surface 39 and/or guide surface 41 is opened in a spatial direction other than that in the above described embodiments. In this case the sliding surface 39 and/or guide surface 41 is opened in a longitudinal direction of the main part 12 and the moveable part 14. Therefore, as is shown in FIG. 20 it is made possible for a closed external side 36 of the main part 12 and moveable part 14 to be formed. The recess 37 formed through this in a longitudinal direction of the main part 12 and the moveable part 14 is constructed as a channel 52, of which a cross-section is shown in FIG. 21, for example. A rear view of the moveable part 14 and the main part 12 is represented in FIG. 22. This recess 37 extends from a proximal end to distal end of the surgical instrument 11 or proximal end of the moveable part 14 and main part 12 to the distal end of the moveable part 14 and main part 12. According to the representation in FIG. 21, the recess 37 has a roof-like shape, or constitutes a triangular shaped recess 37. The same is valid for the recess 37 in the main part 12. These recesses 37 in the main part and moveable part extend to the guides 27, so that these regions can also be cleaned on cleaning with a cleaning agent.

Alternative to the embodiment represented, a recess 37 can be provided either only in the moveable part 14 or only in the main part 12, or alternately with at least a small overlap in each case. In each external edge region of the moveable part 14 and of the main part 12, as shown in FIG. 21, a narrow gap 42 between the remaining sliding surface 39 and guide surface 41 is formed. The gap 42 is again washable from the inside out. Equally, it can be intended that a bevel 43 can again be arranged on the parting plane on the external side, on one side or mirror-inverted, in each case on the parting plane between the sliding surface 39 and the guide surface 41.

So that a cleaning inside of the input region in this embodiment is also possible, it is particularly intended that at least the indentation 39 or the pilot pin 31 features a recess 37 extending in a longitudinal direction. Preferably the indentation 39 as well as the pilot pin 31 features a recess 37, so that this region can also be cleaned. This is shown as an example in FIG. 21.

The invention claimed is:

1. Surgical instrument, in particular a sliding shaft instrument, comprising:
a main part and a relative moveable part,
with a handle arranged on the main part, the former having a fixed grip and a grip for actuating the moveable part,
with at least one guide through which the moveable part relative to the main part is moveable between an initial position and a working position, and
the moveable part is guiding at the distal end with a hinge joint,
the moveable part having a sliding surface pointing to the main part and also having a pair of side surfaces extending upwardly from the sliding surface from a proximal end of the sliding surface to a distal end of the sliding surface, the main part having a guide surface pointing to the sliding surface and also having a pair of side surfaces extending downwardly from the guide surface from a proximal end of the guide surface to a distal end of the guide surface, the sliding surface being slidable along the guide surface, whereby
the sliding surface and the guide surface are arranged at least partially with each other for the formation of a washable gap, and
that, by angling the side surfaces of at least one of the main part and the moveable part, at least the sliding surface or the guide surface is reduced transversely to the longitudinal direction of the moveable part and the main part to a width or
at least the sliding surface or the guide surface is opened by at least one recess extending transversely from one of the side surfaces to the other of the side surfaces of at least one of the main part and moveable part, improving the formation of the gap between the sliding surface and the guide surface for the cleaning of the surgical instrument.

2. Surgical instrument according to claim 1, whereby on an external side of the main part or the moveable part, or on an external side of the main part and the external side of the moveable part, a bevel is provided bordering the guide surface or sliding surface, which is sloped in at least portions to the longitudinal centre line of the main part and the moveable part.

3. Surgical instrument according to claim 1, whereby a bevel is provided on each external side of the main part and the moveable part, bordering the sliding surface and bordering the guide surface.

4. Surgical instrument according to claim 3, whereby the bevel is constructed mirror-symmetrically about the longitudinal centre line of the moveable part and main part, or mirror-symmetrically about the gap.

5. Surgical instrument according to claim 1, whereby on only one external side of the sliding surface or the guide surface, or on an external side of the sliding surface and bordering the guide surface, a bevel is provided, which extends substantially over the whole width of the moveable part or main part.

6. Surgical instrument according to claim 1, whereby at least the sliding surface or the guide surface is opened by a recess extending in a longitudinal direction of the main part and moveable part.

7. Surgical instrument according to claim 6, whereby the recess is formed in an undulating, triangular, rectangular, trapezoidal, hemispherical or sawtooth form.

8. Surgical instrument according to claim 6, whereby the recess is formed by two elevations arranged neighbouring each other, in truncated cone form, in frustropyramidal form, in hemispherical form, or in the form of a crescent segment.

9. Surgical instrument according to claim 1, whereby at least one recess or a bevel borders a guide.

10. Surgical instrument according to claim 9, whereby the recess or bevel is formed by a T-shaped indentation and a pilot pin, or by a hinge joint.

* * * * *